(12) United States Patent
Demopulos et al.

(10) Patent No.: US 6,740,100 B2
(45) Date of Patent: May 25, 2004

(54) TENDON REPAIR USING ADHESIVE

(75) Inventors: Gregory A. Demopulos, Mercer Island, WA (US); Scott W. Reed, Monroe, CT (US); Alan B. Bachman, Milford, CT (US); Frederick T. Karl, Newtown, CT (US); William J. Allen, Stratford, CT (US); Leland Ray Adams, Ansonia, CT (US); G. Lawrence Thatcher, Chelmsford, MA (US)

(73) Assignee: Omeros Corporation, Seattle, WA (US)

( * ) Notice: Subject to any disclaimer, the term of this patent is extended or adjusted under 35 U.S.C. 154(b) by 195 days.

(21) Appl. No.: 10/112,597

(22) Filed: Mar. 28, 2002

(65) Prior Publication Data

US 2002/0161400 A1 Oct. 31, 2002

Related U.S. Application Data

(63) Continuation of application No. PCT/US00/35261, filed on Dec. 22, 2000.
(60) Provisional application No. 60/171,963, filed on Dec. 23, 1999.

(51) Int. Cl.⁷ .............................................. A61B 17/04
(52) U.S. Cl. ...................................................... 606/152
(58) Field of Search ......................................... 606/152

(56) References Cited

U.S. PATENT DOCUMENTS 3,176,316 A    4/1965   Bodell
3,716,058 A    2/1973   Tanner
3,833,002 A    9/1974   Palma
3,842,441 A    10/1974  Kaiser
3,960,152 A    6/1976   Augurt et al.
3,987,497 A    10/1976  Stoy et al.
3,991,766 A    11/1976  Schmitt et al.

(List continued on next page.)

FOREIGN PATENT DOCUMENTS

EP      0520177 A1       12/1992
SU      566575           8/1977
WO      WO 01/28457 A1   4/2001

OTHER PUBLICATIONS

Sanders, D.W., et al., "Cyclic Testing of Flexor Tendon Repairs: an In Vitro Biomechanical Study," *J. Hand Surg.* 22:1004–1010 (1997).

Norris et al., "Flexor Tendon Suture Methods: a Quantitative Analysis of Suture Material within the Repair Site," *Orthopedics* 22:413–416 (1999).

Radford et al., "Immediate Strength After Suture of a Torn Anterior Cruciate Ligament," *J. Bone Joint Surg.* 76:480–484 (1994).

(List continued on next page.)

*Primary Examiner*—Gary Jackson
(74) *Attorney, Agent, or Firm*—Marcia S. Kelbon

(57) ABSTRACT

A reinforcing member or stent (7) is inserted into opposite end portions (1, 1') of a lacerated tendon and secured within the tendon by adhesive so that tension applied to the tendon is transmitted across the laceration by way of the reinforcing member (7).

19 Claims, 3 Drawing Sheets

U.S. PATENT DOCUMENTS

| | | |
|---|---|---|
| 4,501,029 A | 2/1985 | McMinn |
| 4,512,038 A | 4/1985 | Alexander et al. |
| 4,534,349 A | 8/1985 | Barrows |
| 4,653,489 A | 3/1987 | Tronzo |
| 4,662,884 A | 5/1987 | Stensaas et al. |
| 4,873,976 A | 10/1989 | Schreiber |
| 4,979,956 A | 12/1990 | Silvestrini |
| 5,047,030 A | 9/1991 | Draenert |
| 5,061,281 A | 10/1991 | Mares et al. |
| 5,061,283 A | 10/1991 | Silvestrini |
| 5,147,362 A | 9/1992 | Goble |
| 5,254,132 A | 10/1993 | Barley et al. |
| 5,350,798 A | 9/1994 | Linden et al. |
| 5,354,305 A | 10/1994 | Lewis et al. |
| 5,425,766 A | 6/1995 | Bowald |
| 5,458,636 A | 10/1995 | Brancato |
| 5,612,052 A | 3/1997 | Shalaby |
| 5,653,769 A | 8/1997 | Barley et al. |
| 5,723,008 A | 3/1998 | Gordon |
| 5,800,544 A | 9/1998 | Demopulos et al. |
| 5,811,091 A | 9/1998 | Greff et al. |
| 5,900,245 A | 5/1999 | Sawhney et al. |
| 5,998,472 A | 12/1999 | Berger et al. |
| 6,001,345 A | 12/1999 | Askill et al. |
| 6,048,343 A | 4/2000 | Mathis et al. |
| 6,080,192 A | 6/2000 | Demopulos et al. |
| 6,083,244 A | 7/2000 | Lubbers et al. |
| 6,102,947 A | 8/2000 | Gordon |
| 6,106,556 A | 8/2000 | Demopulos et al. |
| 6,214,012 B1 | 4/2001 | Karpman et al. |

OTHER PUBLICATIONS

Lazovic et al., "Collagen Repair Not Improved by Fibrin Adhesive. Cruciate Ligament Ruptures Studied in Dogs," *Acta Orthop. Scand.*64:583–586 (1993).

Potenza, Austin D., "Tendon Healing Within the Flexor Digital Sheath in the Dog," *The Journal of Bone and Joint Surgery* 44–A:49–64 (1962).

Allan et al., "Evaluation of Adhesive and Absorption Properties for Absorbable Tissure Adhesives," *Unpublished Work*(2000).

Shalaby et al., "Controlling the Adhesion of Polymers to Soft and Hard Tissues," *Proc. 21st Meeting, Adhesion Society*, Feb. 22–25 (1998).

Kline et al., "A Model Test Method for Evaluation of Absorbable Tissue Adhesives," *Trans. Sixth World Biuomater. Cong., III*, 1062 (2000).

Dayal et al., "The Effect of pH on Absorbable Tissue Adhesive Strengths," *Trans. Sixth World Biuomater. Cong., III*, 1070 (2000).

Hinds, et al., "A Bilaminar Elastin Patch Deployed with a Bioabsorbable Cyanoacrylate to Repair," *Trans. Sixth World Biuomater. Cong., III*, 1060 (2000).

Allan et al., "In vitro and In vivo Screening of New Compliant Absorbable Hemostatic Tissue Adhesives," *Trans. Sixth World Biuomater. Cong., III*, 318 (2000).

Flagle et al., "Absorbable Tissue Adhesives in Skin Wound Repair," *Trans. Soc. Biomater.*, 22:376 (1999).

Allan et al., "Absorbable Gel Forming Sealants/Adhesives as a Staple Adjuvant in Wound Repair," *Trans. Soc. Biomater.*, 22:374 (1999).

Flagle et al., "In vitro Evaluation of Absorbable Tissue Adhesives," *Trans. Soc. Biomater.*, 22:376 (1999).

Bionx Implants, Inc., "Bionx Implants—Meniscus Arrow," www.bionximplants.com (Internet Access Date: Oct. 15, 2002).

Mitek Products, "Mitek—Meniscal Repair System," www.jnjgateway.com (Internet Access Date Jun. 20, 2000).

Arthrotek a Biomet Company, "Arthrotek—Meniscal Staple," *Pamphlet*(2002).

Peretti et al., "Tissue Engineered Implant for Meniscus Repair," *Report*(2002).

Arthrex, "Arthrex Surgical Techniques," www.arthrex.com (Internet Access Date Jun. 20, 2000).

Sherman et al., "The Long–Term Followup of Primary Anterior Cruciate Ligament Repair. Defining a Rationale for Augmentation," *Am. J. Sports Med.*19:243–255 (1991).

Richards, H.J., "Repair and Healing of the Divided Digital Flexor Tendon," *Injury*12:1–12 (1980).

Becker, H., "Primary Repair of Flexor Tendons in the Hand without Immobilisation–Preliminary Report," *Hand*10:37–47 (1978).

Silfverskiold et al., "Two New Methods of Tendon Repair: an In Vitro Evaluation of Tensile Strength and Gap Formation," *J. Hand Surg.*18:58–65 (1993).

Strickland, J., "Flexor Tendon Repair: Indiana Method," et seq., *The Indiana Hand Center Newsletter*, 1:1–20 (1993).

"Sports, Orthopedic and Rehabilitation Medicine Associates—Torn Meniscus," www.soarmedical.com (Internet Access Date: Jun. 28, 2000).

TENDON REPAIR USING ADHESIVE

CROSS-REFERENCE TO RELATED APPLICATIONS

The present application is a continuation of International Application PCT/US00/35261 filed Dec. 22, 2000 designating the United States, which claims the benefit of the filing date of U.S. Provisional Application Serial No. 60/171,963 filed Dec. 23, 1999.

FIELD OF THE INVENTION

The present invention relates to a system for repairing lacerated or severed soft tissue structures of the body, particularly connective cords such as tendons.

BACKGROUND OF THE INVENTION

Repair techniques for lacerated or severed tendons vary widely depending on the nature of the injury and the particular tendon affected. There are large differences in the extent to which access can be obtained in the least obtrusive manner, in the amount of tendon excursion, in the surrounding environment, in the stresses to which different tendons are normally subjected, and in the healing characteristics of different tendons. In addition, often there is no consensus of the overall best way to repair a given tendon.

For example, repair of a long flexor tendon in the hand that has been severed is typically achieved by suturing the severed tendon ends face-to-face. Historically, the joints across which the tendon acts were immobilized for from three to eight weeks to protect the tendon while it healed, because a freshly sutured tendon can withstand only a fraction of the tensile force to which a healthy tendon is subjected during normal use. Immobilization results in scarring and adhesion formation along the length of the tendon. Range of motion is adversely affected, particularly in the case of flexor tendons which normally glide smoothly through and over the unique system of tendon tunnels and pulleys of the hand. Nevertheless, it was thought that fibroblastic ingrowth was required in order for the tendon to heal, such that immobilization and the resulting decreased range of motion were considered necessary evils in order for effective healing to take place. More recently it has been discovered that flexor tendons have an intrinsic capacity to heal and that early motion may actually expedite healing. Still, exercises must be carefully planned and carried out due to the weakness of the sutured repair. In early stages of healing, protected passive and/or restricted active exercises may be used, followed by tendon gliding and active strengthening exercises in later stages. The affected joints are most often partially immobilized to prevent inadvertent application of excess force.

SUMMARY OF THE INVENTION

The present invention is concerned with a system for repair of injured soft tissue structures, particularly connective cords such as tendons, by use of adhesive and, preferably, reinforcing members or stents which can be made of substantially rigid or semi-rigid material. Such stents are adapted for extending longitudinally between severed end portions of a tendon with the severed end portions in abutting relationship. The tendon is secured to the stent by the adhesive such that tension applied to the tendon is transmitted through the stent. The stent and adhesive maintain the severed tendon ends abutting as tension is applied to the tendon.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
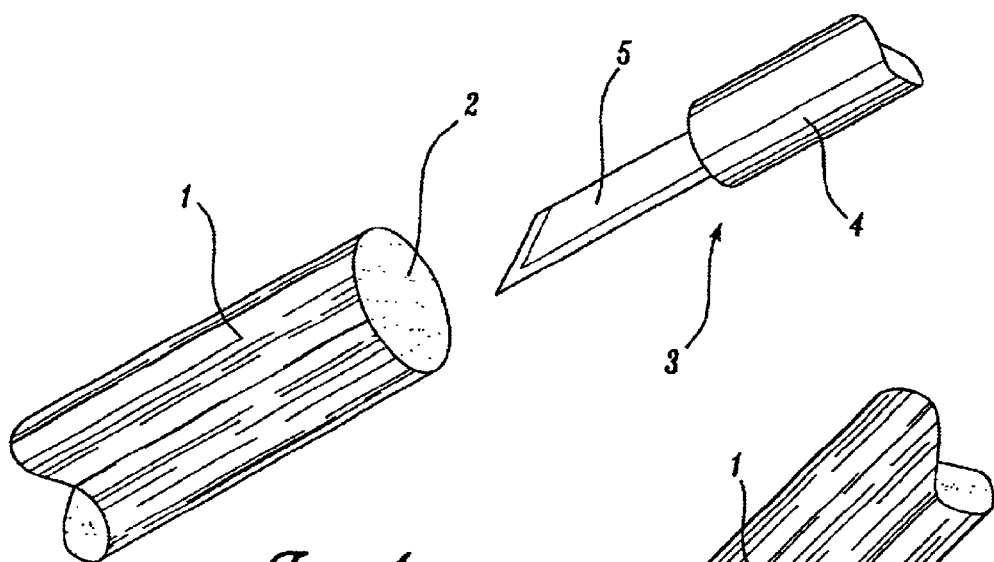
FIG. 1 is a diagrammatic top perspective of a severed end of a tendon and a cutting tool that can be used to prepare a tendon for repair using the present invention.

The present invention provides a splice for soft tissue structure having a laceration. FIG. 1 shows a tendon 1 severed at a lacerated "end" face 2. In preparation for insertion of a reinforcing member or stent, a cutting tool 3 having a handle 4 and distally projecting blade 5 can be used to cut a slit 6 (FIG. 2) in the end face 2 of the tendon 1. Preferably the slit does not extend the full width of the tendon, so that the external sheath of the tendon is not weakened. The same procedure can be used for forming a slit in the mating tendon end portion 1' (see FIG. 2).

Figure 2:
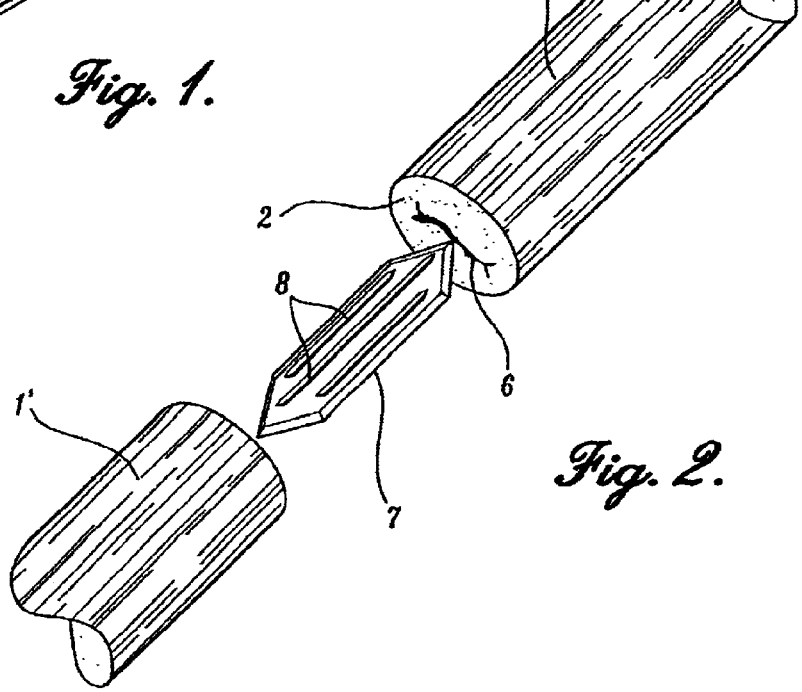
FIG. 2 is a top perspective corresponding to FIG. 1 showing a severed tendon is the process of repair in accordance with the present invention.
Figure 3:
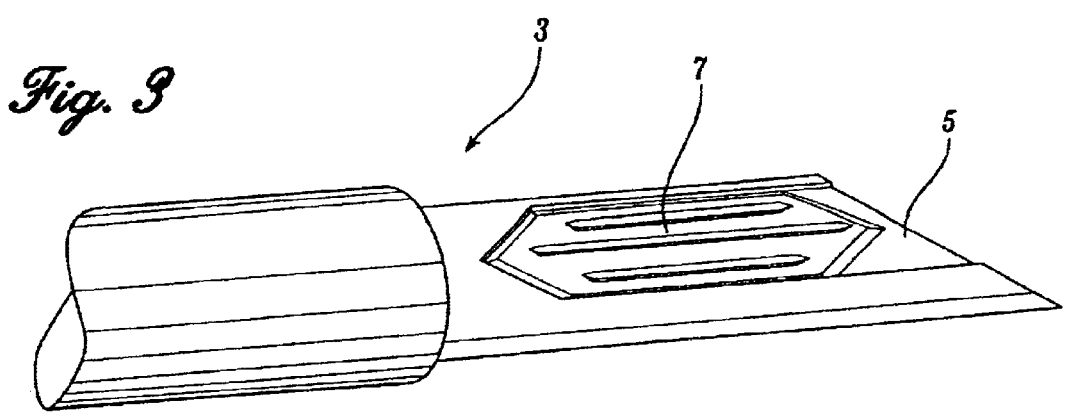
FIG. 3 is a top perspective of another tool that can be used when repairing a tendon in accordance with the present invention.

Next, a reinforcing member or stent 7 is inserted into first one then the other slit 6, and the end faces of the severed tendon 1, 1' are brought together to an abutting relationship. The stent 7 shown in FIG. 2 is much longer than it is wide and much wider than it is thick, having opposite broad surfaces at the top and bottom. More specifically, the width of the stent is approximately equal to the width of the preformed slits 6, and the length of the stent is approximately equal to the depth of the slits measured axially or lengthwise of each tendon portion 1, 1'. The stent may be inserted by use of a suitable grasping tool, eased by forming the stent with pointed and/or sharpened ends. Alternatively, as represented diagrammatically in FIG. 3, the blade 5 of the cutting tool 3 can be formed with a depression for receiving the stent 7. By careful manipulation of the cutting tool, the stent may be automatically deposited in a first end portion 1, 1' of the tendon as the cutting tool is removed following formation of the slit 6. Another alternative is to form the slit with one tool, and deposit the stent with another tool similar to that shown in FIG. 3.

Ultimately, the stent will be held in place within the slits 6 by adhesive. To increase the surface area between the stent, the adhesive and the tendon, and to form channels for receiving the adhesive, the stent 7 of FIG. 2 may have longitudinally extending grooves 8 or other surface modifications to expand surface area in both its upper and lower surfaces. These grooves may extend all the way through the stent, but preferably extend only partway into the stent to isolate the top surface from the bottom.

Figure 4:
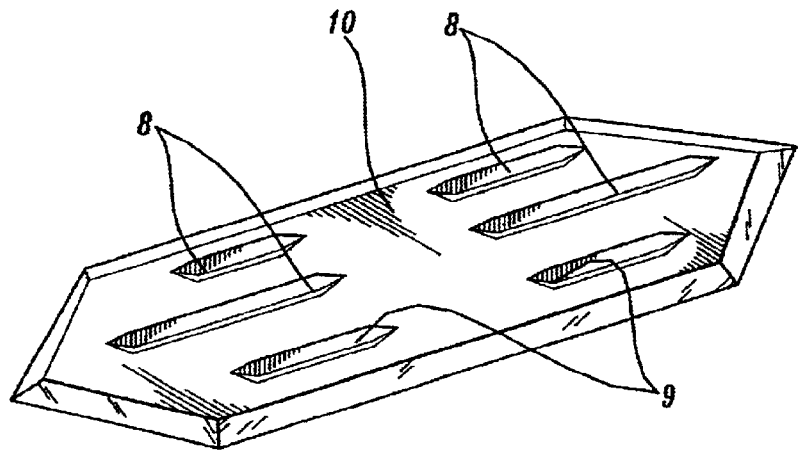
FIG. 4 is a top perspective of a first embodiment of a stent usable in the present invention.

With reference to FIG. 4, it may be desirable to prevent the adhesive from flowing between the abutting faces of the severed tendon. Consequently, the grooves 8 can have inner ends 9 which are spaced apart, such that an ungrooved area 10 is formed at the center of the stent, both in the top and bottom surfaces, in the area where the stent bridges between the abutting faces of the severed tendon.

Figure 5:
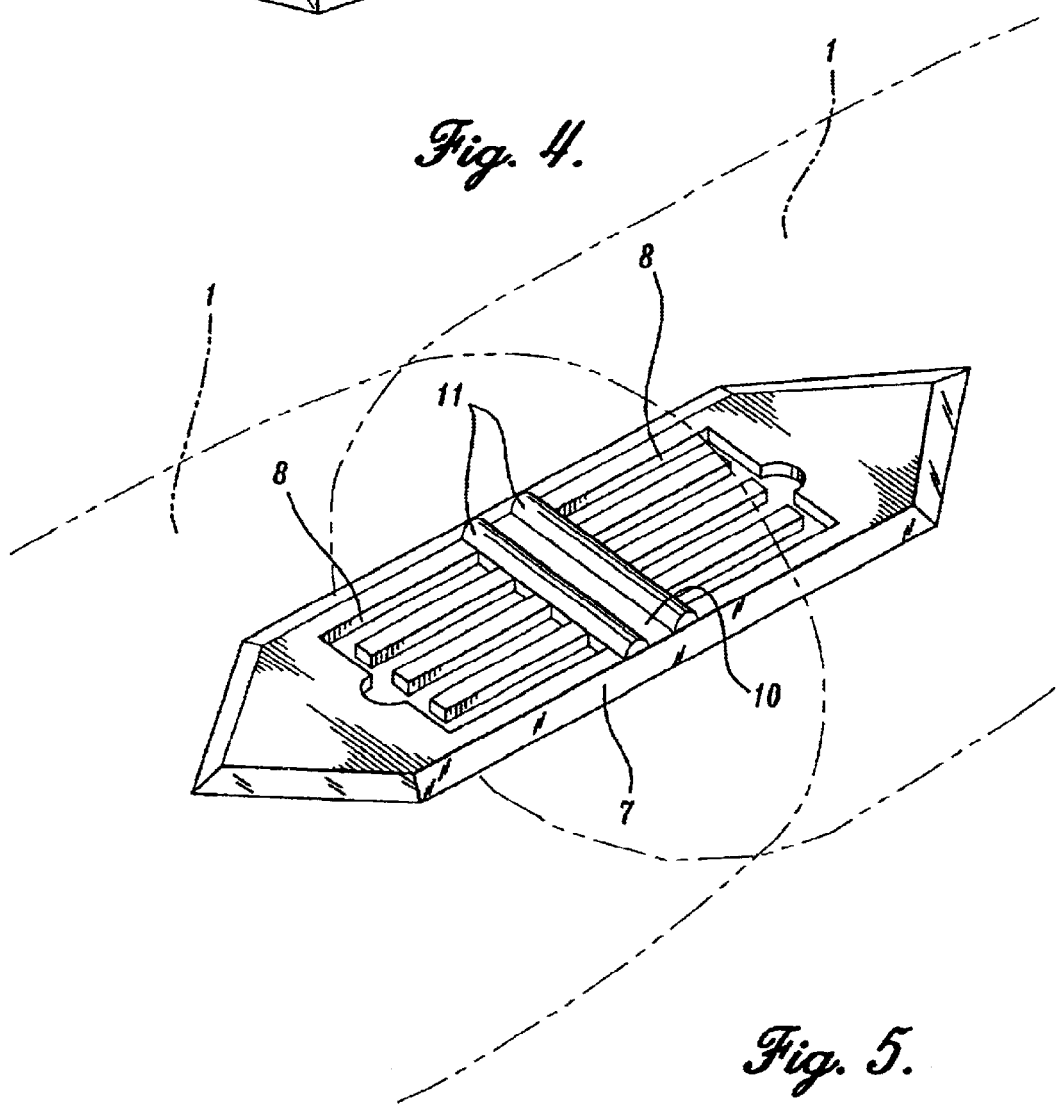
FIG. 5 is an enlarged top perspective of a second embodiment of a stent usable in the present invention.

FIG. 5 shows another construction in more detail, including a pattern of grooves 8 at the opposite end portions of the stent 7. At each end the grooves are in communication with each other, but the grooves at one end are not in communication with the grooves at the other. Short bumps 11 can be formed at the inner ends of the grooves 8 at each end, to further isolate the central portion 10 from the grooves and, preferably, prevent adhesive from flowing to the abutting faces of the severed tendon. While the grooves 8 can be formed in only one or the other of the flat surfaces of the stent 7, preferably the grooves are formed both at the top and at the bottom.

Figure 6:
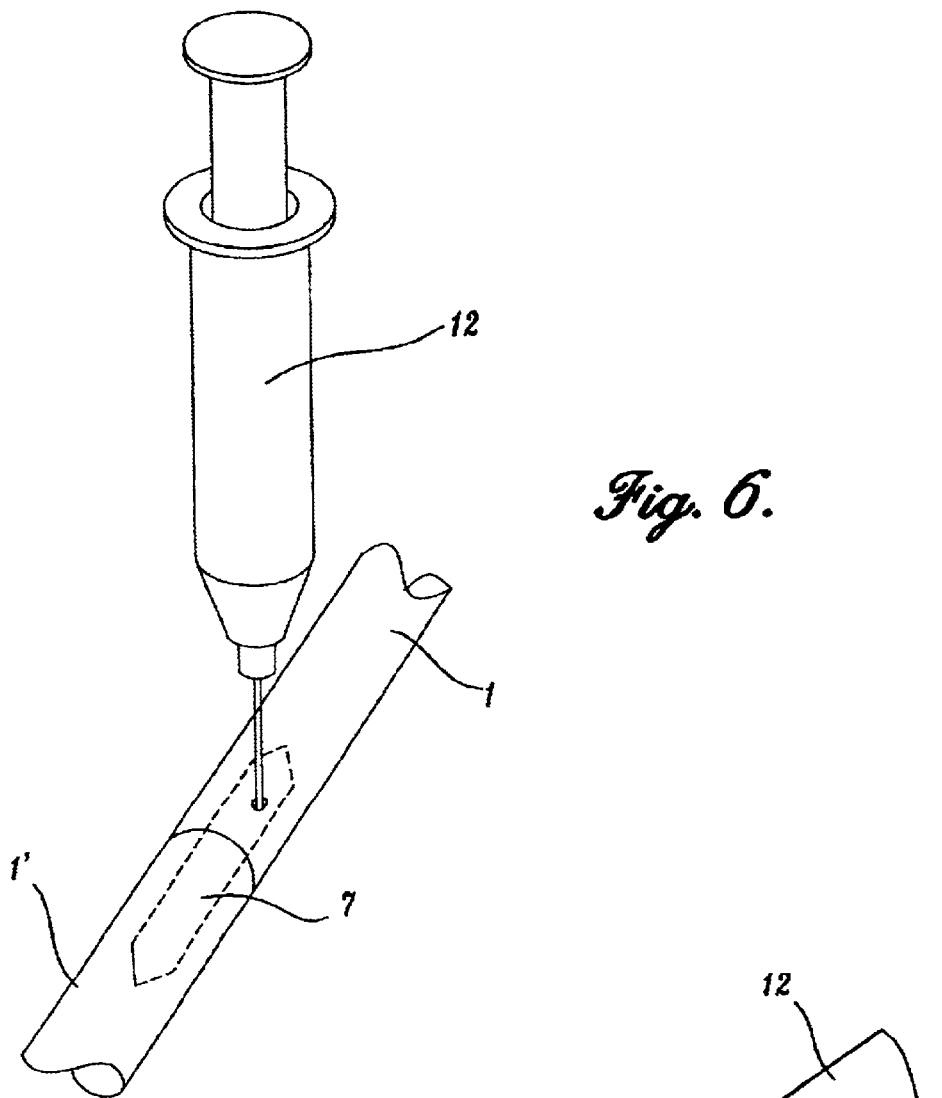
FIG. 6 is a diagrammatic top perspective of a severed tendon in the proces of repair in accordance with the present invention.
Figure 7:
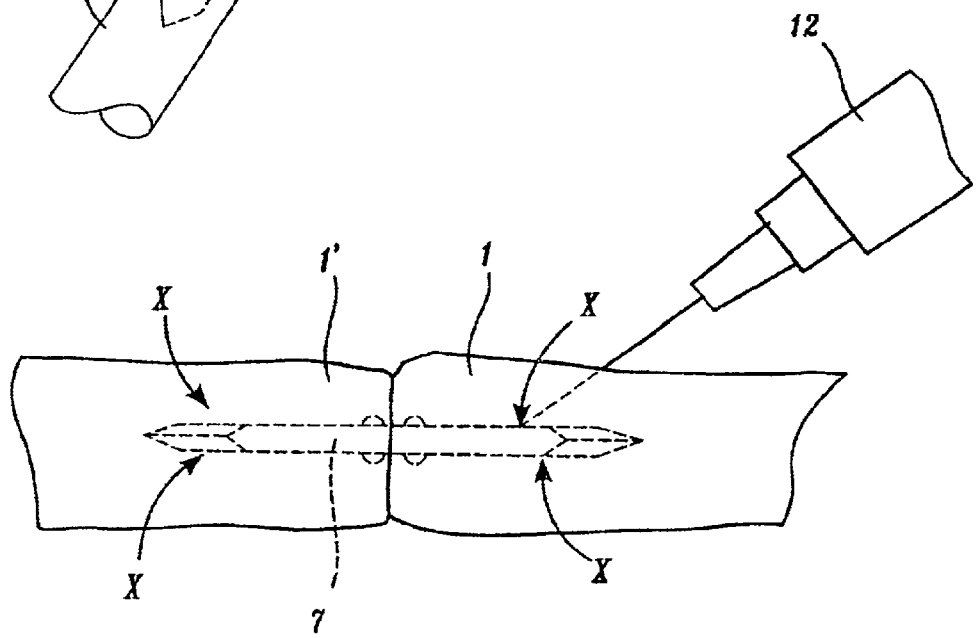
FIG. 7 is side elevation of the repair of FIG. 6, with parts broken away.

With reference to FIG. 6 and FIG. 7, a settable liquid adhesive is used to fix the stent within the slits of the severed tendon end portions 1, 1'. One way this can be done is by use of a syringe 12. For consistent results, the amount of adhesive is predetermined, i.e., a "metered" amount of injected adhesive is used. As illustrated diagrammatically in FIG. 7, the adhesive can be injected by use of the syringe at a plurality of sites along the stent (e.g., four locations designated "x", two at each end, one of which is at the top surface and the other of which is at the bottom surface). In addition, to provide additional strength of the repair and a smooth outer profile of the repaired tendon, a metered quantity of an adhesive can be carefully applied externally around the area of the abutting faces of the severed tendon, preferably without injecting or disbursing that adhesive between the severed ends which could interfere with healing.

Preferably the stent will be dimensionally stable so that once it is secured in place it will not elongate or stretch which could alter the abutting relationship of the severed tendon ends and interfere with healing. Nevertheless, the stent should be reasonably flexible, possibly approaching the flexibility of the tendon itself, so as not to interfere with excursion of the tendon during normal motion. This may require that the stent be very thin. Widthwise and lengthwise, the stent has substantial dimensions for increasing the effective surface area for bonding the stent internally of the tendon by use of the adhesive.

It is envisioned that the adhesive can be of the general type described in U.S. Pat. No. 5,350,798 of Linden et al. or a variant. Such an adhesive is, in general, a polymer gel and, more specifically, a cyanoacrylate polymer. Modified gels are described in U.S. Pat. Nos. 5,714,159 and 5,612,052 of Shalaby.

At the time of injection, preferably the adhesive flows freely without high adhesive properties relative to the tendon, but will thereafter set quickly and secure the severed tendon ends in the desired abutting relationship. The adhesive preferably will have a high sheer strength and approximately the same bending and deflection characteristics as the stent, i.e., the adhesive, once set, will not stretch substantially and also will not be so rigid as to crack if the repaired tendon undergoes normal deflection. The adhesive may inherently have disinfectant characteristics and/or may be coated or impregnated with a compound having disinfectant characteristics. Alternatively or additionally, the adhesive may serve as a delivery system for drugs and/or agents and/or factors to promote healing and/or growth. Both the stent and the adhesive preferably are bioabsorbable, but over a sufficiently long length of time that full healing of the tendon occurs. Materials currently under consideration for the stent are E-caprolactone and poly-L-lactide, or a blend or co-polymer of E-caprolactone and/or trimethylene carbonate and poly-L-lactide, preferably with an inherent viscosity in the range of 1.0 to 2.8 dL/gm at 20° C. These polymers also may be optimized to meet the physical requirements of a successful tendon repair, such as by controlling the degree of crystallinity via primary and/or secondary processing conditions. In general, it is preferred that the strength of the stent-adhesive repair plus the strength of the healed or partially healed tendon be equal or greater to that necessary for full active motion of the tendon. For example, in the case of a flexor tendon of the hand, the stent-adhesive repair may provide "full" strength for approximately three weeks and at least about 50% strength at six weeks when the partially healed tendon itself has 50% or more of its normal tensile strength.

For a typical repair of a flexor tendon of the hand, the width of the stent could be about 3 mm, the length about 2 to 3 cm and the thickness about 0.7 mm in order to withstand a force of 5000 to Department of Biomedical Engineering 720 Rutland Avenue Baltimore, Md. 21205-2196 6500 grams without substantial stretching or elongation. This results in a bonding area at each side of at least about 3 mm by 10 mm at both the top surface and the bottom surface, although the actual size of the bonding area will depend on the design of the stent. The bond strength at each of the four bonding areas (top and bottom at each side of the tendon laceration) is preferably at least about 2500 to about 3250 grams.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A splice for soft tissue structure having a laceration forming adjacent lacerated surfaces, said splice comprising an elongated reinforcing member and a quantity of adhesive, the reinforcing member being substantially longer than it is wide and substantially wider than it is thick defining opposite broad surfaces, the reinforcing member being sized for insertion into the soft tissue structure in an orientation extending across the laceration with the lacerated surfaces abutting and being adapted for being secured inside the soft tissue structure by the quantity of adhesive such that tension applied to the soft tissue structure is transmitted through the reinforcing member.

2. A splice for a tendon normally tensioned in the body during joint movement and having a laceration forming adjacent lacerated ends, said splice comprising an elongated reinforcing member and a quantity of adhesive, the reinforcing member being substantially longer than it is wide and substantially wider than it is thick defining opposite broad surfaces, the reinforcing member being sized for insertion into the tendon in an orientation extending across the laceration with the lacerated ends abutting and being adapted for being secured inside the tendon without penetrating the circumferential sheath of the tendon by the quantity of adhesive for tension applied to the tendon being transmitted through the reinforcing member.

3. The splice of claim 2, in which the reinforcing member is dimensionally stable in the direction of its length so as not to stretch during normal tensioning of the tendon.

4. The splice of claim 3, in which the reinforcing member is flexible in a direction transverse to its length about an axis extending widthwise of the reinforcing member.

5. The splice of claim 3, in which at least one of the broad opposite surfaces of the reinforcing member has a plurality of grooves for increasing the surface area of such surface.

6. The splice of claim 2, in which opposite end portions of the broad opposite surfaces of the reinforcing member have grooves for increasing the respective surface areas of such end portions, the reinforcing member having an ungrooved central portion positioned to be located in the area of abutting lacerated ends of the tendon.

7. The splice of claim 2, in which at least one of the broad opposite surfaces includes a central portion positioned to be aligned with the abutting lacerated ends of die tendon and enlargements formed at opposite sides of the central portion to prevent flow of adhesive into the central portion.

8. The splice of claim 2, in which the reinforcing member has sharpened opposite ends.

9. The splice of claim 2, in which the reinforcing member has pointed opposite ends.

10. A repair comprising a soft tissue structure having abutting lacerated surfaces, an elongated internal reinforcing member bridging across the abutting lacerated surfaces and extending into the portions of the soft tissue structure adjacent to the lacerated surfaces, a quantity of adhesive securing opposite end portions of the reinforcing member in the portions of the soft tissue structure adjacent to the lacerated surfaces such that tension applied to the soft tissue structure is transmitted across the abutting surfaces by way of the reinforcing member, the reinforcing member being dimensionally stable in the direction of its length so as not to stretch upon application of normal tension to the soft tissue structure.

11. A repair comprising a tendon having abutting lacerated ends, an elongated internal reinforcing member bridging across the abutting lacerated ends and extending into the adjacent tendon end portions without penetrating the circumferential sheath of the tendon, a quantity of adhesive securing opposite end portions of the reinforcing member in the opposite lacerated end portions at opposite sides of the abutting ends such that tension applied to the tendon is transmitted across the abutting ends by way of the reinforcing member, the reinforcing member being dimensionally stable in the direction of its length so as not to stretch upon application of normal tension to the tendon.

12. The repair of claim 11, in which the adhesive and reinforcing member are bioabsorbable over a period of time at least as great as the normal period for healing of the abutting lacerated ends.

13. The repair of claim 11, in which the adhesive is a cyanoacrylate polymer.

14. The repair of claim 11, in which the adhesive has disinfectant characteristics.

15. The repair of claim 11, in which the adhesive contains an agent to promote healing.

16. A repair comprising an elongated internal reinforcing member that is installed to bridge across abutting lacerated surfaces of a soft tissue structure and extending into the portions of the soft tissue structure adjacent to the lacerated surfaces, and a quantity of adhesive securing opposite end portions of the reinforcing member in the portions of the soft tissue structure adjacent to the lacerated surfaces such that tension applied to the soft tissue structure is transmitted across the abutting surfaces by way of the reinforcing member, the reinforcing member being dimensionally stable in the direction of its length so as not to stretch upon application of normal tension to the soft tissue structure.

17. A method of repairing a lacerated soft tissue structure having respective lacerated surfaces which comprises inserting a reinforcing member into the portions of the soft tissue structure adjacent to the lacerated surfaces, positioning the lacerated surfaces in abutting relationship, and securing the reinforcing member in the soft tissue structure by adhesive.

18. A method of repairing a lacerated tendon having respective lacerated end faces which comprises inserting a reinforcing member into the lacerated end portions of the tendon, positioning the lacerated end races in abutting relationship, and securing the reinforcing member in the tendon by adhesive.

19. The method of claim 18, including securing the reinforcing member in the lacerated end portions of the tendon by injecting adhesive through a needle at multiple locations adjacent to opposite end portions of the reinforcing member.

\* \* \* \* \*

UNITED STATES PATENT AND TRADEMARK OFFICE
CERTIFICATE OF CORRECTION

PATENT NO.    : 6,740,100 B2
DATED         : May 25, 2004
INVENTOR(S)   : Gregory Demopoulos et al.

It is certified that error appears in the above-identified patent and that said Letters Patent is hereby corrected as shown below:

<u>Column 4,</u>
Lines 24-26, "a force of 5000 to Department of Biomedical Engineering
            720 Rutland Avenue
            Baltimore, Md. 21205-2196 6500 grams without
            substan-" should read -- a force of 5000 to 6500 grams without substan- --

<u>Column 5,</u>
Line 15, "die" should read -- the --

<u>Column 6,</u>
Line 35, "races" should be -- faces --

Signed and Sealed this

Ninth Day of November, 2004

JON W. DUDAS
*Director of the United States Patent and Trademark Office*